(12) United States Patent
Sasaki et al.

(10) Patent No.: US 8,013,108 B2
(45) Date of Patent: Sep. 6, 2011

(54) PROCESS FOR PRODUCING 2, 3, 3', 4',-BIPHENYLTETRACARBOXYLIC DIANHYDRIDE

(75) Inventors: Kenichiro Sasaki, Ube (JP); Tatsushi Nakayama, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 324 days.

(21) Appl. No.: 12/171,093

(22) Filed: Jul. 10, 2008

(65) Prior Publication Data
US 2009/0018349 A1 Jan. 15, 2009

(30) Foreign Application Priority Data
Jul. 12, 2007 (JP) ................... 2007-183361

(51) Int. Cl.
*C08G 69/26* (2006.01)
*C07C 65/00* (2006.01)

(52) U.S. Cl. ...................................... 528/353; 562/888
(58) Field of Classification Search .................. 528/353; 562/888
See application file for complete search history.

(56) References Cited

U.S. PATENT DOCUMENTS
4,958,002 A 9/1990 Imatani et al.
2006/0247445 A1 11/2006 Nakayama et al.

*Primary Examiner* — Taylor Victor Oh
(74) *Attorney, Agent, or Firm* — Knobbe Martens Olson & Bear LLP

(57) ABSTRACT

2,3,3',4'-biphenyltetracarboxylic acid is heat-dehydrated in a molten state at a temperature not lower than 200° C. in a flow of an inert gas in a reactor 10 having at least one reaction vessel 11 by stirring the molten material to produce 2,3,3',4'-biphenyltetracarboxylic dianhydride. Thus obtained 2,3,3',4'-biphenyltetracarboxylic dianhydride in the molten state is subsequently cooled and solidified in an inert gas or dry air, or cooled and solidified in the ambient air at a temperature of 40° C. or lower or 100° C. or higher.

16 Claims, 3 Drawing Sheets

To the solidification step

PROCESS FOR PRODUCING 2, 3, 3', 4',-BIPHENYLTETRACARBOXYLIC DIANHYDRIDE

FIELD OF THE INVENTION

The present invention relates to a process for producing 2,3,3',4'-biphenyltetracarboxylic dianhydride useful as a source material of polyimide in high purity and good efficiency.

BACKGROUND ART 3,4,3',4'-biphenyltetracarboxylic dianhydride (hereinafter, may be abbreviated as s-BPDA) and 2,3,3',4'-biphenyltetracarboxylic dianhydride (hereinafter, may be abbreviated as a-BPDA) are each known as a monomer source material for producing aromatic polyimide. In particular, a polyimide produced from s-BPDA as a monomer component is superior in properties such as heat resistance, electrical insulation, film strength, film dimensional stability, solvent resistance and the like. Accordingly, because of a high demand for s-BPDA, an efficient process for producing a high purity s-BPDA has been intensively investigated.

On the other hand, even if polymerized with the same aromatic diamine, a-BPDA and s-BPDA produce polyimides having entirely different properties. Hence, as to a-BPDA, a high-purity product containing no s-BPDA is needed.

U.S. Pat. No. 4,958,002 (Patent Reference 1) describes a process for obtaining s-BPDA by dehydrating 3,4,3',4'-biphenyltetracarboxylic acid (hereinafter, may be abbreviated as s-BPTA) in a nitrogen atmosphere at a temperature up to about 280° C. as final stage. In this process, dehydration progresses while crystalline state is maintained during the process. Since a crystalline-powdery product is thus obtained, a highly-pure product can be efficiently produced.

On the other hand, in terms of production of a-BPDA, the present applicant proposed a process for obtaining highly-pure and powdery a-BPDA by dehydrating 2,3,3',4'-biphenyltetracarboxylic acid (hereinafter, may be abbreviated as a-BPTA) in inert gas atmosphere at a temperature from 180 to 195° C. in JP-A-2006-328040 (Patent Reference 2). Since, this process aims at obtaining a powdery product, however, the process is essentially for a batch operation and is not so suitable for a continuous operation.

As an example for obtaining a-BPDA by a dehydration reaction in a molten state, Patent Reference 2 describes an example using a hot-air-circulating type heater (see the comparative example 2 in Patent Reference 2). Since a usual hot-air-circulating type heater utilizes a tray, this method is also for a batch operation. Although a continuous hot-air-circulating type heater is also available, it has partially open portions and, therefore it has a defect in that sublimates are prone to form and oxidation-degradation of highly-reactive anhydrides (a-BPDA) are prone to take place.

Furthermore, the evaluation by the present inventors revealed that a product suitable for producing polyimide is difficult to produce by the production of a-BPDA in the case of conducting a dehydration reaction in a molten state. In the case of the production of s-BPDA, there is no defect in the quality of the anhydride obtained even if the dehydration reaction is carried out in a molten state by melting the raw material on a tray under a nitrogen atmosphere. In the case of the production of a-BPDA, however, if the dehydration reaction was carried out in a molten state by melting the raw material on a tray under a nitrogen atmosphere, a-BPDA of high quality is not obtained; that is, high-molecular-weight polyamic acid (i.e., polyimide precursor) was not easily obtained from the a-BPDA obtained.

Patent Reference 1: U.S. Pat. No. 4,958,002
Patent Reference 2: JP-A-2006-328040 (US-2006-0247445 A1)

SUMMARY OF THE INVENTION

The present invention has been made in view of this problem, and an objective of the present invention is to provide a process for producing highly-pure 2,3,3',4'-biphenyltetracarboxylic dianhydride (a-BPDA) suitable for production of high-molecular-weight polyimide in good productivity.

The present invention relates to a process for producing 2,3,3',4'-biphenyltetracarboxylic dianhydride, comprising a dehydration step of heat-dehydrating 2,3,3',4'-biphenyltetracarboxylic acid in a molten state at a temperature not lower than 200° C. under a flow of an inert gas in a reactor having at least one reaction vessel by (i) stirring the molten material, or (ii) bubbling the molten material by passing the inert gas; thereby, producing 2,3,3',4'-biphenyltetracarboxylic dianhydride.

The present invention also relates to a process for producing 2,3,3',4'-biphenyltetracarboxylic dianhydride, comprising:

cooling and solidifying a molten 2,3,3',4'-biphenyltetracarboxylic dianhydride in an inert gas or dry air; or cooling and solidifying a molten 2,3,3',4'-biphenyltetracarboxylic dianhydride in the ambient air at a temperature of 40° C. or lower or 100° C. or higher. This solidification process is preferably applied as the process for solidifying 2,3,3',4'-biphenyltetracarboxylic dianhydride obtained particularly by previously-described process, i.e., by the heat-dehydration in a molten state at a temperature not lower than 200° C. in a flow of an inert gas in a reactor having at least one reaction vessel by (i) stirring the molten material, or (ii) bubbling the molten material by passing the inert gas.

According to the present invention, there is provided a process for producing highly-pure 2,3,3',4'-biphenyltetracarboxylic dianhydride (a-BPDA) suitable for production of high-molecular-weight polyimide in good productivity.

Figure 1:
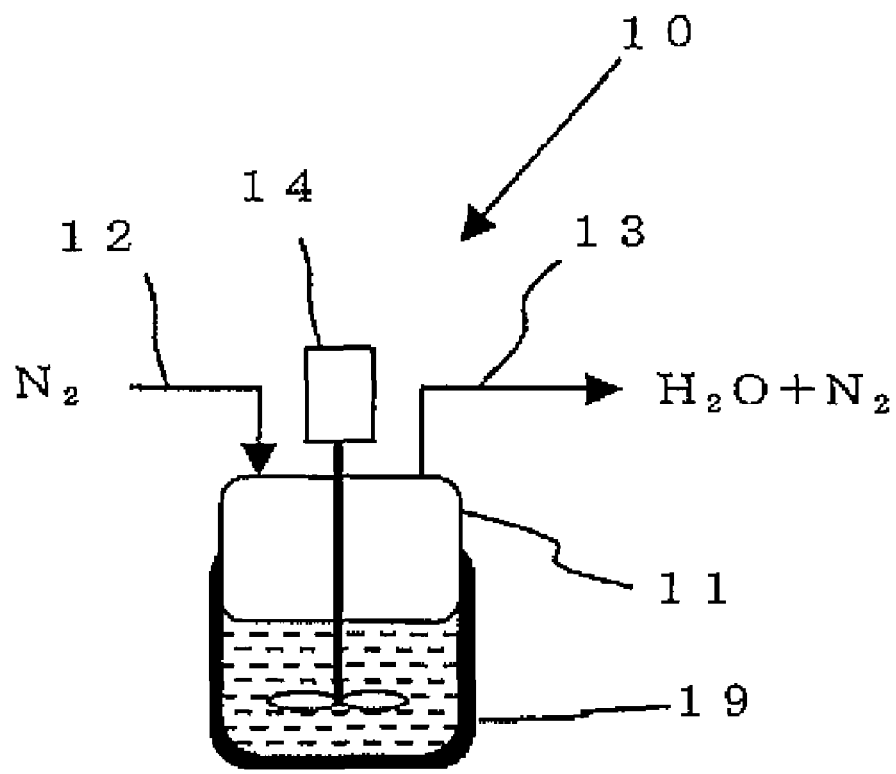
FIG. 1 is a figure schematically showing an example of the reactor used for the dehydration reaction.

Explanation of symbols; 10: reactor, 11: reaction vessel, 12: gas introducing pipe, 13: gas exhaust pipe, 14: stirrer, 19: heater, 20: reactor, 21a: first reaction vessel, 21b: second reaction vessel, 22a and 22b: gas introducing pipe, 23a and 23b: gas exhaust pipe, 24a and 24b stirrer, 25: pouring inlet of a-BPTA, 26: extracting outlet of reactant, 27: receiving inlet of reactant, 28: extracting outlet of product, 29a and 29b: heater, 50: drum dryer, 51: box, 52: introducing inlet of molten a-BPDA, 53: gas introducing pipe, 54: cooling drum, 55: scraping board, 56: rotary valve, 57: outlet.

DETAILED DESCRIPTION OF THE INVENTION

The major abbreviations used in the present invention are as follows.
a-BPTT: 2,3,3',4'-biphenyltetracarboxylic acid tetraester s-BPTT: 3,4,3',4'-biphenyltetracarboxylic acid tetraester
a-BPTA: 2,3,3',4'-biphenyltetracarboxylic acid
s-BPTA: 3,4,3',4'-biphenyltetracarboxylic acid
a-BPDA: 2,3,3',4'-biphenyltetracarboxylic dianhydride
s-BPDA: 3,4,3',4'-biphenyltetracarboxylic dianhydride In the following explanation, both types of nomenclatures may be mentioned together as necessary.

The disclosure of the present application as a whole is summarized as follows.

1. A process for producing 2,3,3',4'-biphenyltetracarboxylic dianhydride, comprising a dehydration step of:
heat-dehydrating 2,3,3',4'-biphenyltetracarboxylic acid in a molten state at a temperature not lower than 200° C. in a flow of an inert gas in a reactor having at least one reaction vessel by (i) stirring the molten material, or (ii) bubbling the molten material by passing the inert gas; thereby, producing 2,3,3',4'-biphenyltetracarboxylic dianhydride.

2. A process according to the above-mentioned item 1, wherein during the dehydration step, the 2,3,3',4'-biphenyltetracarboxylic acid is continuously supplied to the reactor, and the resultant 2,3,3',4'-biphenyltetracarboxylic dianhydride in a molten state is continuously taken out of the reactor.

3. A process according to the above-mentioned item 2, wherein the reactor comprises a plurality of reaction vessels serially connected.

4. A process according to one of the above-mentioned items 1 to 3, wherein an average reaction time of the dehydration step is not shorter than 2 hours.

5. A process according to one of the above-mentioned items 1 to 4, wherein an average residence time in a single of the reaction vessels is not longer than 6 hours.

6. A process according to one of the above-mentioned items 1 to 5, further comprising a solidification step wherein the molten 2,3,3',4'-biphenyltetracarboxylic dianhydride is received from the dehydration step; and is subsequently cooled and solidified in an inert gas or dry air, or cooled and solidified in the ambient air at a temperature of 40° C. or lower or 100° C. or higher.

7. A process according to the above-mentioned item 6, wherein the molten 2,3,3',4'-biphenyltetracarboxylic dianhydride is continuously received and continuously supplied to a solidifying apparatus to give a solid 2,3,3',4'-biphenyltetracarboxylic dianhydride.

8. A process according to the above-mentioned item 7, wherein the solidifying apparatus comprises a cooling surface, and the molten 2,3,3',4'-biphenyltetracarboxylic dianhydride is cooled on the cooling surface.

9. A process according to one of the above-mentioned items 6 to 8, wherein the cooled and solidified 2,3,3',4-biphenyltetracarboxylic dianhydride is pulverized to give a powder having a median size less than 100 µm.

10. A process according to one of the above-mentioned items 1 to 9, wherein a water content of the 2,3,3',4'-biphenyltetracarboxylic acid to be supplied to the dehydration step is not higher than 10%.

11. A process for producing 2,3,3',4'-biphenyltetracarboxylic dianhydride, comprising:
cooling and solidifying a molten 2,3,3',4'-biphenyltetracarboxylic dianhydride in an inert gas or dry air; or
cooling and solidifying a molten 2,3,3',4'-biphenyltetracarboxylic dianhydride in the ambient air at a temperature of 40° C. or lower or 100° C. or higher.

12. A process according to one of the above-mentioned items 1 to 10, wherein the obtained 2,3,3',4'-biphenyltetracarboxylic dianhydride is polymerized with 4,4'-diaminodiphenyl ether at an equal mole in a solvent of N-methyl-2-pyrrolidone at a monomer concentration of 10% by mass at 25° C. for 4.5 hours, to give a polyamic acid having a logarithmic viscosity not less than 1.0, wherein the logarithmic viscosity is measured in a solution of N-methyl-2-pyrrolidone at a concentration of 0.5 g/100 ml at 30° C.

13. 2,3,3',4'-biphenyltetracarboxylic dianhydride produced by the process according to one of the above-mentioned items 1 to 11, wherein
the 2,3,3',4'-biphenyltetracarboxylic dianhydride is polymerized with 4,4'-diaminodiphenyl ether at an equal mole in a solvent of N-methylpyrrolidone at a monomer concentration of 10% by mass at 25° C. for 4.5 hours, to give a polyamic acid having a logarithmic viscosity not less than 1.0, wherein the logarithmic viscosity is measured in a solution of N-methyl-2-pyrrolidone at a concentration of 0.5 g/100 ml at 30° C.

The present invention is explained in details as follows.

<Dehydration Step>

The dehydration step is the step where a-BPTA (2,3,3',4'-biphenyltetracarboxylic acid) is dehydrated by heating to produce a-BPDA (2,3,3',4'-biphenyltetracarboxylic dianhydride).

The a-BPTA supplied to the dehydration step, as described in, for example, JP-A-2006-328040 (Patent Reference 2), may be produced by the hydrolysis of a-BPTT (2,3,3',4'-biphenyltetracarboxylic acid tetraester) which is obtained by the dimerization reaction of o-phthalic acid diester as a starting material. Highly-pure a-BPTA may be obtained by using known procedures of isolation and purification such as distillation or crystallization during each step of the reaction. Preferably, a-BPTA should be sufficiently dried before supplied to the dehydration step, i.e., it is preferably dried so that its water content is not more than 10% by mass, particularly preferably not more than 5% by mass. For example, the powdery a-BPTA obtained in the previous step by hydrolysis followed by crystallization is dried for example, under ambient-pressure or reduced pressure at 50 to 180° C. preferably for about 1 to 20 hours for example, using a mixer such as Henschel mixer.

In particular, as a step after the dimerization reaction of o-phthalic acid diester as a starting material, the process preferably comprises a series of steps of (1) obtaining a-BPTT crystals having a purity of 95% or higher (preferably 98% or higher, particularly 99% or higher) by a crystallization operation, (2) hydrolyzing under pressure with heat preferably using neither acid nor alkali, (3) obtaining a-BPTA preferably by crystallization, (4) reducing the water content preferably to 10% or less, particularly to 5% or less, and (5) afterward supplying to the dehydration step.

The present invention is conducted in a molten state at a temperature not lower than 200° C. in a flow of an inert gas by (i) stirring the molten material, or (ii) bubbling the molten material by passing the inert gas. In the present invention, it is considered extremely important to force the molten mixture to flow so as to contact with the inert gas, and to allow moisture (i.e. water) in the molten mixture to diffuse in the inert gas. In case that a-BPTA in the molten state is not stirred or bubbled, separation into a white crystalline region and a transparent noncrystalline region was observed in the solidified material of the a-BPDA cooled after complete reaction. As the result of the water content measurement by the Karl Fischer's method, it was confirmed that the a-BPDA in the noncrystalline region contains more moisture (i.e. higher water content) in comparison with the crystalline region (noncrystalline region: water content 0.1 to 0.15% or more; crystalline region: water content 0.01 to 0.02%). It was also confirmed that high-molecular-weight polyamic acid (polyimide precursor) cannot be obtained from the obtained a-BPDA (see the example).

On the other hand, even if the production of s-BPDA was carried out by conducting the dehydration of the s-BPTA in flow of the nitrogen without stirring in the molten state heated to 310° C., noncrystalline region was not present in the obtained s-BPDA after cooled and solidified. That is to say, it is obvious that the generation of the noncrystalline region and the quality deterioration is the problem specific to the production of the a-BPDA.

As a reactor for the dehydration reaction, a tank-type reactor having at least one reaction vessel may be used. FIG. 1 schematically shows an example of the reactor. This reactor 10 is a batch-type reactor and it is equipped with a reaction vessel 11, a gas introducing pipe 12, a gas exhaust pipe 13, a stirrer 14, and a heater 19.

Using a reactor like this, while introducing the nitrogen gas (inert gas) from the gas introducing pipe 12 and circulating it in the reactor, the heat-dehydration reaction is carried out by heating the a-BPTA, up to a temperature of 200° C. or higher, preferably 210° C. or higher, preferably not higher than 300° C., more preferably not higher than 250° C., to give molten state, and stirring the molten mixture by the stirrer 14. The water generated from the dehydration reaction (i.e., water-elimination reaction) is discharged outside the system from the gas exhaust pipe 13 as accompanied by the nitrogen gas.

In this figure, the method of stirring the molten mixture was shown as a method for fluidizing the molten mixture so as to bring it contact with the inert gas. However, the method of bubbling the molten mixture by passing the inert gas may also be used. Also, the method of bubbling with the inert gas with simultaneously stirring the molten mixture may be used.

As the inert gas, a gas not reacting with a-BPTA or a-BPDA is used. From a viewpoint of cost, nitrogen is preferable. The inert gas is leastwise required not to contain oxygen; the inert gas containing a little of moisture is acceptable as long as it can be accompanied by the water generated in the dehydration reaction and can discharge the water outside the system.

The stirrer may be those in the form leastwise capable of stirring a liquid material while passing the inert gas, i.e., those in the form leastwise capable of stirring without impeding the inert gas introduction and gas exhaust. For example, a rotary-type stirrer equipped with stirring wings, a shaking-type stirrer, and a homo-mixer are exemplified. Also, the faster the stirring speed is, in the shorter time the dehydration reaction is completed. The stirring speed and rotation speed may be appropriately chosen by considering the shape of the stirring wings and so on.

A continuous operation may be possible using the reactor shown in FIG. 1 which is further equipped with a pouring inlet from which a-BPTA can be continuously poured, and an extracting outlet from which the reactant can be continuously taken out.

In the present application, the term "molten 2,3,3',4'-biphenyltetracarboxylic dianhydride" or "molten a-BPDA" is used in meanings encompassing not only the pure molten material of a-BPDA but the molten reaction product obtained from the dehydration reaction of a-BPTA. When, in particular, conducting a continuous operation, as a characteristic of a tank-type reaction vessel, its reaction time is an average residence time, therefore, unreacted a-BPTA may be contained.

Figure 2:
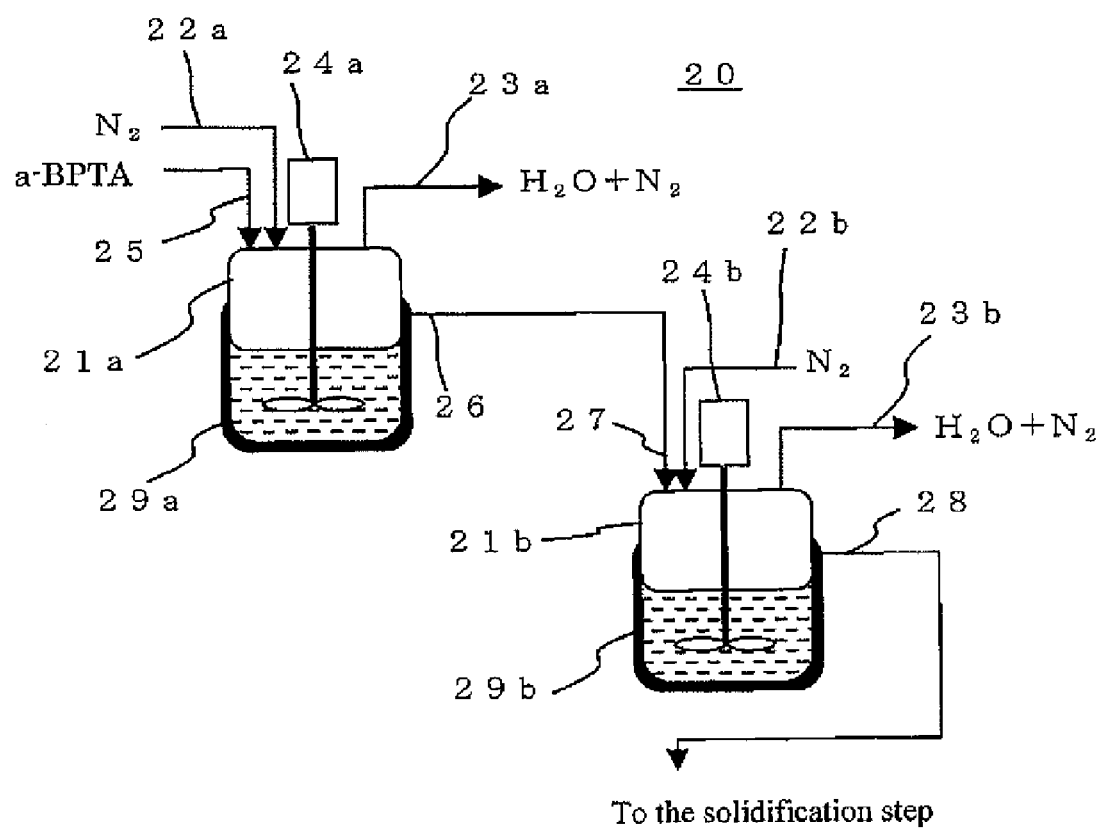
FIG. 2 is a figure schematically showing an example of the reactor used for the dehydration reaction for a continuous operation.

As a reactor usable for the reaction, an apparatus having two or more reaction vessels capable of stirring the molten mixture and/or bubbling with the inert gas is also preferable. FIG. 2 shows a reactor 20 equipped with two reaction vessels. The first upstream reaction vessel 21a is equipped with a gas introducing pipe 22a, a gas exhaust pipe 23a, a stirrer 24a, and a heater 29a, in addition, a pouring inlet 25 of the source material a-BPTA and an extracting outlet 26 of the reactant. The second downstream reaction vessel 21b is equipped with a gas introducing pipe 22b, a gas exhaust pipe 23b, a stirrer 24b, and a heater 29b, in addition, a receiving inlet 27 of the reactant from the first reaction vessel and an extracting outlet 28 of the product. The extracting outlet 26 of the reactant of the first reaction vessel 21a and the receiving inlet 27 of the reactant of the second reaction vessel 21b are connected through a pipe (equipped with a pump as necessary), which allows the transfer of the molten reactant from the first reaction vessel to the second reaction vessel.

The source material a-BPTA is continuously supplied from the pouring inlet 25 to the first reaction vessel 21a, and it is heated, melted, and stirred by the stirrer 24a. The dehydration reaction progresses by heating for a given average residence time at a given temperature, and the most part is converted to a-BPDA. The molten mixture is taken out from the extracting outlet 26. As an extracting method (i.e. method of taking out), the reactant may be extracted by overflowing, or a predetermined amount may be continuously extracted by a pump.

The reaction mixture extracted from the first reaction vessel is continuously introduced to the second reaction vessel 21b from the receiving inlet 27 of the reactant, and it is heated for a given average residence time at a given temperature, and the unreacted a-BPTA is dehydrated to convert to a-BPDA. The reactant is finally taken out from the extracting outlet 28. During the dehydration reaction, the water generated in the first reaction vessel 21a and the second reaction vessel 21b is respectively discharged from the gas exhaust pipes 23a and 23b as accompanied by the inert gas introduced from the gas introducing pipes 22a and 22d.

Since the serial connection of two or more reaction vessels reduces the unreacted a-BPTA and allows the production of the highly-pure a-BPDA with good production efficiency, it is particularly suitable for the continuous operation. Since too many numbers of the reaction vessels makes the apparatus large, in general, the number is preferably not more than 5, more preferably not more than 4, and most preferably 2 or 3.

The reaction time of the dehydration step is preferably not shorter than 2 hours, generally not longer than 30 hours, preferably not longer than 20 hours, more preferably not longer than 10 hours. Since in the present invention the reaction effectively progresses even in a short time, a reaction time not longer than 8 hours, not longer than 6 hours, furthermore not longer than 5 hours may be acceptable. In the case of a continuous operation, the average residence time of the reactant is preferably set to this time. In the case that the plurality of the reaction vessels is used, the sum of the residence time in each reaction vessel is preferably set to this time. In the case of the continuous operation, it is also preferable that the average residence time in one reaction vessel is not longer than 6 hours, furthermore not longer than 5 hours.

<Solidification Step>

The solidification step is a step to cool and solidify the molten a-BPDA. The solidification step in the present invention is per se a distinctive procedure. Therefore, the a-BPDA in the molten state to be supplied to the solidification step may be a-BPDA produced by any procedure. Preferably, it is the molten a-BPDA obtained from the dehydration of a-BPTA according to the present invention, as previously-described. In particular, the molten reaction product continuously extracted in the dehydration step is preferably continuously supplied to the solidification step.

During the solidification step of the present invention, the molten a-BPDA is either (i) cooled and solidified in the inert gas or dry air, or (ii) cooled and solidified in the ambient air at a temperature of 40° C. or lower or 100° C. or higher. Here, the term "ambient air" means the general ambient atmosphere, and more specifically an ambient air having a relative humidity from 10 to 70%, preferably from 10 to 60%. The term "dry air" means an air having a reduced humidity by dehumidification and an air having a relative humidity preferably less than 10%, more preferably less than 5%, furthermore preferably less than 2%, the most preferably less than 1%. The inert gas used in the present invention also preferably has humidity of these levels, including from the preferable level to the most preferable level as mentioned above.

In the case of s-BPDA, i.e. the isomer, quality deterioration, such as the generation of the noncrystalline region, was not observed even when the molten material at 310° C. was cooled and solidified in the ambient air at 80° C. In the case of the a-BPDA, however, the generation of the noncrystalline region was observed when it was cooled at about 80° C. (see examples). Surprisingly, the noncrystalline region was not generated when the molten a-BPDA was cooled and solidified in the inert gas or dry air, or cooled and solidified in the ambient air at a temperature of 40° C. or lower or 100° C. or higher.

Any inert gas may be available as long as it does not degrade a-BPDA, and from a viewpoint of cost, nitrogen is preferable.

Since, as the product, the powder is preferable due to handling, the flaky product formed by cooling and solidifying is preferably further pulverized to give its powder.

Figure 3:
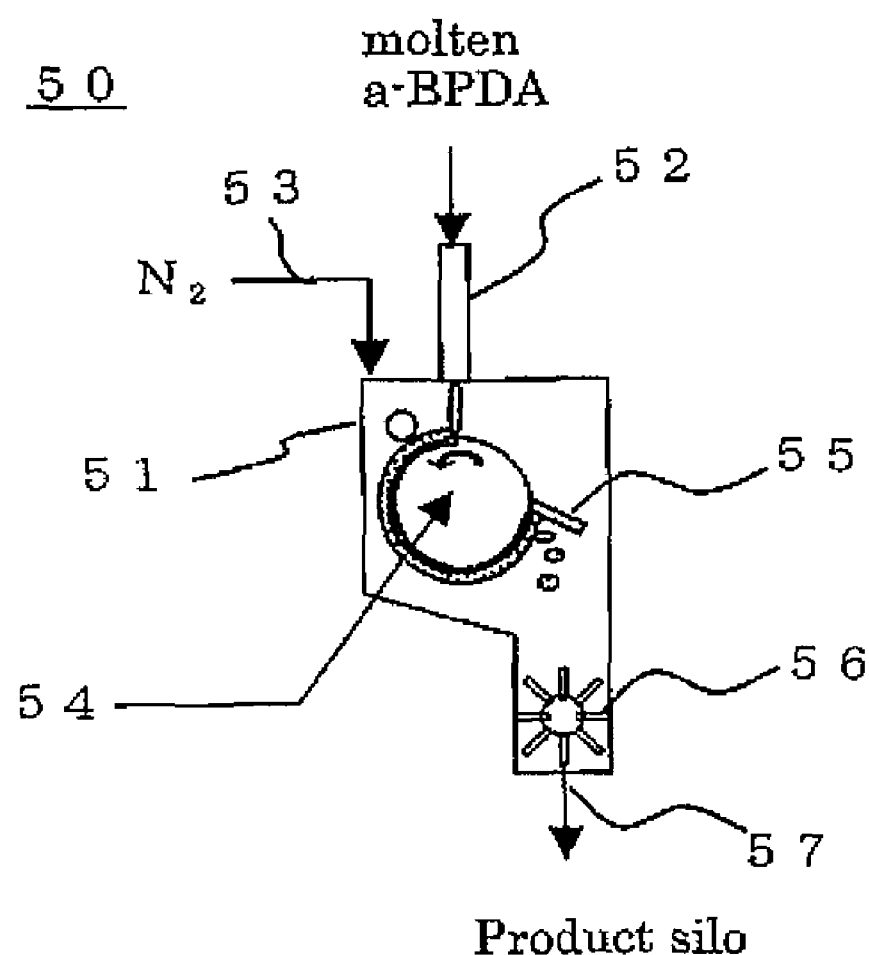
FIG. 3 is a figure schematically showing an example of the solidifying apparatus used for the solidification step.

FIG. 3 shows a drum dryer as an example of the apparatus preferably used for the solidification step of the present invention. The drum dryer 50 has the introducing inlet 52 of the molten a-BPDA and does the cooling drum 54 in the box 51 equipped with the gas introducing pipe 53. The molten a-BPDA is introduced from the introducing inlet 52 to the inside of the drum dryer and allowed to flow on the cooling drum 54 which is maintained at a predetermined temperature and rotating; and the a-BPDA is cooled on the cooling drum 54 and solidified in the form of a thin film. The solidified a-BPDA is rotated with the drum and scraped off from the cooling drum by the scraping board 55. Since the flaky solid forms, this is easily pulverized in later steps and the powdery material is obtained as the final product easy to handle. The flaky solid, after scraped off from the cooling drum, drops down, passes through the rotary valve 56, goes outside from the outlet 57, and is further pulverized as necessary and stored in a silo etc as the powdery product.

The atmosphere in the box 51 during cooling may be set by introducing into the box 51 the inert gas or dry air from the gas introducing pipe 53. When cooling is carried our in the ambient air (ambient atmosphere), no gas is introduced, or the ambient air is introduced from the gas introducing pipe 53. The rotary valve is located at the outlet 57 and carries the inert gas or dry air etc. in the apparatus with the flaky solid to the outside of the apparatus, and it is designed to prevent the outside gas from commingling into the apparatus.

The regulation of the cooling temperature is carried out by setting the temperature of the cooling drum 54. The surface of the cooling drum is preferably a metal such as, for example, stainless steel. For the cooling temperature, a temperature not higher than the melting point of the a-BPDA is selected, preferably not higher than 170° C., more preferably not higher than 150° C., furthermore preferably not higher than 140° C. Since it is not necessary to cool beyond necessity, it is generally not lower than 0° C., preferably not lower than 10° C., more preferably not lower than 20° C. When cooling and solidifying is carried in the ambient air, in addition to these preferable condition, a temperature range of "40° C. or lower or 100° C. or higher" must be fulfilled.

In any case in the inert gas or dry air, or the ambient air, for cooling and solidifying on the cooling drum surface, a relatively smaller difference of the cooling temperature is preferable so as to prevent repelling on the cooling drum surface. Therefore, the most preferable cooling temperature is within a range of 100° C. or higher.

Also, using this apparatus, the flaky solid is roughly pulverized when it passes through the rotary valve 56. As necessary, it is further pulverized by using a pulverizer such as, for example, a cutter mill, a roller mill, Henschel mixer and the like to make a median size less than 100 μm, preferably less than 50 μm. Generally, the median size is 3 μm or larger. The product having this particle size provides the ease of handling, good process-adaptability and process-compatibility when producing the polyamic acid.

For the continuous manufacture, the molten a-BPDA may also be continuously supplied from the dehydration step to the solidification step, for example, by directly connecting the extracting outlet 28 of the reactor 20 shown in FIG. 2 and the introducing inlet 52 of the solidifying apparatus 50 with a pipe.

As the cooling apparatus, an apparatus having a cooling surface is preferable. While FIG. 3 shows an apparatus having a drum as a cooling member, other apparatus, such as a belt-flaker having a movable belt as a cooling member, or a table-flaker having a table as a cooling member and a scraping mechanism, are also usable.

EXAMPLES

Next, the present invention will be more specifically explained by the examples.

<Method for Measurement of the Logarithmic Viscosity (η) of the Polyamic Acid>

The "polyamic acid obtained under the standard condition" refers to the polyamic acid obtained by polymerizing a-BPDA and 4,4'-diaminodiphenyl ether at an equal mole at a monomer concentration of 10% by mass in N-methylpyrrolidone solvent at 25° C. for 4.5 hours. In each example and comparative example, a sample a-BPDA was polymerized under the standard condition. A solution of the polyamic acid (a solution of 0.5 g/100 ml of N-methyl-2-pyrrolidone) is prepared, and the time (t1) taken for the solution to pass between the upper line and the lower line by using the Cannon-Fenske viscometer at 30° C. is measured, and subsequently, the time (t0) taken for the solvent alone to pass is measured. The logarithmic viscosity (η) of the polyamic acid is represented by the following expression.

$$\text{Logarithmic viscosity} = \{\ln(t1/t0)\}/\text{solution concentration},$$

wherein, ln denotes natural logarithm.

The particle size of the a-BPDA powder was measured by dispersing the power with the use of water as a dispersion medium by a ultrasonic wave, and using a laser diffraction/scattering particle size distribution measuring instrument (model: LA-910, Laboratories Co., Ltd.).

Example 1

The pre-drying of the a-BPTA having a purity of 99.5% was carried out by the Henschel mixer to obtain the a-BPTA powder having a water content (water of crystallization) of about 5%. This a-BPTA 250 g was charged into a glass separable flask having a stirrer. The dehydration reaction in the molten state was carried out by circulating nitrogen at 50 mL/min. and stirring at a temperature of 220° C. at a rotation speed of 300 rpm for 4 hours. The reactant was transferred into a stainless-steel vat at the room temperature (25° C.) to obtain 214 g of the clumped a-BPDA. The a-BPDA pulverized by a mortar was polymerized with diaminodiphenyl ether in N-methylpyrrolidone solvent for 4.5 hours to obtain the "polyamic acid obtained under the standard condition." The logarithmic viscosity (η) at a concentration of 0.5 g/100 mL showed a high value of 1.44.

Examples 2 to 4

The a-BPDA was obtained in a similar manner to that of the example 1 except that the conditions shown in Table 1 were applied as the dehydration reaction condition. The viscosities of the polyamic acid obtained under the standard condition were shown in Table 1. The conditions and results were shown together with those of the Example 1.

Examples 5 to 8

In the Example 1, the stirring was stopped and alternatively nitrogen was used to bubble. The a-BPDA was obtained in a similar manner to that of the Example 1 except for the conditions shown in Table 1 as the dehydration reaction condition. The viscosities of the polyamic acid obtained under the standard condition were shown in Table 1.

Comparative Examples 1 and 2

The a-BPDA was obtained in a similar manner to that of the Example 1 except that the stirring was stopped and the conditions shown in Table 1 was adopted as the dehydration reaction condition. The viscosities of the polyamic acid obtained under the standard condition were shown in Table 1.

TABLE 1

| | Dehydration reaction condition | | | | |
|---|---|---|---|---|---|
| | Temperature (° C.) | Stirring (rpm) | $N_2$ Blowing (ml/min) | $N_2$ Bubbling (ml/min) | Reaction time (h) | Polyamic acid Viscosity (η) |
| Ex. 1 | 220 | 300 | 50 | 0 | 4 | 1.44 |
| Ex. 2 | 220 | 300 | 50 | 0 | 2 | 1.44 |
| Ex. 3 | 220 | 300 | 50 | 0 | 1 | 1 |
| Ex. 4 | 220 | 120 | 50 | 0 | 4 | 1.22 |
| Ex. 5 | 220 | 0 | 0 | 100 | 4 | 1.45 |
| Ex. 6 | 220 | 0 | 0 | 100 | 2 | 1.44 |
| Ex. 7 | 220 | 0 | 0 | 100 | 1 | 1.32 |
| Ex. 8 | 220 | 0 | 0 | 50 | 4 | 1.42 |
| Comp. Ex. 1 | 220 | 0 | 50 | 0 | 4 | 0.9 |
| Comp. Ex. 2 | 220 | 0 | 50 | 0 | 2 | 0.3 |

<Solidification Experiments>

In the Example 1, the dehydration reaction was carried out by using a 40 L stainless-steel reactor equipped with a jacket, continuously supplying a-BPTA, and continuously extracting the reactant with an average residence time of 4 hours. The other conditions were similarly set to that of the Example 1. The continuous solidification of the obtained a-BPDA molten material (220° C.) was carried out by using a top-feeding type drum dryer (cooling solidification area 0.5 m², made by Mitsubishi Materials Techno Co.) to obtain the flaky a-BPDA.

Experiments were carried out by setting the temperature of the cooling drum and test-atmosphere to the conditions of Table 2, and the results shown in the table were obtained. Polyamic acid obtained under the standard condition from the a-BPDA including no noncrystalline region (noncrystalline region 0%) showed a high logarithmic viscosity (η) of 1.44. The production capacity was also high) i.e., 100 kg/H (2.4 t/day).

TABLE 2

| Solidification condition | | | Properties of the solid material | |
|---|---|---|---|---|
| Temperature of a-BPDA (° C.) | Temperature of cooling drum (° C.) | Test-atmosphere | Crystalline region (%) | Noncrystalline region (%) |
| 220 | 25 | ambient air | 100 | 0 |
| 220 | 40 | ambient air | 100 | 0 |
| 220 | 80 | ambient air | 10 | 90 |
| 220 | 80 | $N_2$ | 100 | 0 |
| 200 | 100 | ambient air | 100 | 0 |
| 220 | 125 | ambient air | 100 | 0 |

From this result, the high-quality a-BPDA with no generation of noncrystalline region was obtained when the cooling temperature was 40° C. or lower or 100° C. or higher in the ambient air. It was found that the $N_2$ ambient is preferable regardless of a temperature because the high quality was accomplished even at 80° C.

Referential Solidification Experiment Example

The molten s-BPDA at 310° C. was solidified in the ambient air with the use of the same apparatus by setting the cooling temperature at 80° C. The obtained solidified material entirely had the crystalline region and the quality deterioration was not observed.

Example 9

Two of 300 L stainless-steel reactor equipped with a jacket were serially connected, the a-BPTA was continuously supplied to the upstream reaction vessel, the molten reactant was conveyed to the second downstream reactor with the average residence time of 4 hours, and the molten product was continuously extracted under the condition where the average residence time in the second reaction vessel is 4 hours. The other conditions were similarly set as Example 1. The extracted a-BPDA was continuously supplied to the top-feeding type drum dryer (the apparatus used for the solidification experiments) and the flaky a-BPDA was continuously obtained. By using the obtained a-BPDA, the viscosity of the polyamic acid obtained under the standard condition showed a high value, i.e., η=1.44. The production capacity was 48 kg/H (1.2 t/day).

Example 10

The pulverization treatment of the flaky a-BPDA obtained by the solidification experiment in the ambient air under the cooling condition of 125° C. was further conducted with the use of a sample mill (made by Kyoristu Riko Ltd.) at 16,000 rpm for 10 minutes to obtain the powdery a-BPDA. The median size of the powder became 63 μm and the handling ability was improved.

INDUSTRIAL APPLICABILITY

The highly-pure a-BPDA can be produced with a good productivity.

What is claimed is:

1. A process for producing 2,3,3',4'-biphenyltetracarboxylic dianhydride, comprising a dehydration step of:
   heat-dehydrating 2,3,3',4'-biphenyltetracarboxylic acid in a molten state at a temperature not lower than 200° C. in a flow of an inert gas in a reactor having at least one reaction vessel by (i) stirring the molten material, or (ii) in bubbling the molten material by passing the inert gas; thereby, producing 2,3,3',4'-biphenyltetracarboxylic dianhydride.

2. A process according to claim 1, wherein during the dehydration step, the 2,3,3',4'-biphenyltetracarboxylic acid is continuously supplied to the reactor, and the resultant 2,3,3',4'-biphenyltetracarboxylic dianhydride in a molten state is continuously taken out of the reactor.

3. A process according to claim 2, wherein the reactor comprises a plurality of reaction vessels serially connected.

4. A process according to claim 1, wherein an average reaction time of the dehydration step is not shorter than 2 hours.

5. A process according to claim 1, wherein an average residence time in a single reaction vessel is not longer than 6 hours.

6. A process according to claim 1, further comprising a solidification step wherein the molten 2,3,3',4'-biphenyltetracarboxylic dianhydride is received from the dehydration step; and is subsequently cooled and solidified in an inert gas or dry air, or cooled and solidified in the ambient air at a temperature of 40° C. or lower or 100° C. or higher, wherein the molten 2,3,3',4'-biphenyltetracarboxylic dianhydride is supplied to a solidifying apparatus comprising a cooling surface and cooled on the cooling surface to give a solid 2,3,3',4'-biphenyltetracarboxylic dianhydride.

7. A process according to claim 6, wherein the molten 2,3,3',4'-biphenyltetracarboxylic dianhydride is continuously received and continuously supplied to the solidifying apparatus.

8. A process according to claim 7, wherein the solidifying apparatus comprises a cooling surface, and the molten 2,3,3',4'-biphenyltetracarboxylic dianhydride is cooled on the cooling surface.

9. A process according to claim 6, wherein the cooled and solidified 2,3,3',4'-biphenyltetracarboxylic dianhydride is pulverized to give a powder having a median size less than 100 µm.

10. A process according to claim 1, wherein a water content of the 2,3,3',4'-biphenyltetracarboxylic acid to be supplied to the dehydration step is not higher than 10%.

11. A process for producing 2,3,3',4'-biphenyltetracarboxylic dianhydride, comprising:
    cooling and solidifying a molten 2,3,3',4'-biphenyltetracarboxylic dianhydride in an inert gas or dry air; or
    cooling and solidifying a molten 2,3,3',4'-biphenyltetracarboxylic dianhydride in the ambient air at a temperature of 40° C. or lower or 100° C. or higher,
    wherein the molten 2,3,3',4'-biphenyltetracarboxylic dianhydride is supplied to a solidifying apparatus comprising a cooling surface and cooled on the cooling surface to give solid 2,3,3',4'-biphenyltetracarboxylic dianhydride.

12. A process according to claim 1, wherein the obtained 2,3,3',4'-biphenyltetracarboxylic dianhydride is polymerized with 4,4'-diaminodiphenyl ether at an equal molar amount in a solvent of N-methyl-2-pyrrolidone at a monomer concentration of 10% by mass at 25° C. for 4.5 hours, to give a polyamic acid having a logarithmic viscosity not less than 1.0, wherein the logarithmic viscosity is measured in a solution of N-methyl-2-pyrrolidone at a concentration of 0.5 g/100 ml at 30° C.

13. A process according to claim 6, wherein the cooled and solidified 2,3,3',4'-biphenyltetracarboxylic dianhydride is in flake form.

14. A process according to claim 6, wherein the temperature of the cooling surface of the solidifying apparatus is 170° C. or lower.

15. A process according to claim 11, wherein the cooled and solidified 2,3,3',4'-biphenyltetracarboxylic dianhydride is in flake form.

16. A process according to claim 11, wherein the temperature of the cooling surface of the solidifying apparatus is 170° C. or lower.

* * * * *

UNITED STATES PATENT AND TRADEMARK OFFICE
CERTIFICATE OF CORRECTION

PATENT NO. : 8,013,108 B2
APPLICATION NO. : 12/171093
DATED : September 6, 2011
INVENTOR(S) : Sasaki et al.

It is certified that error appears in the above-identified patent and that said Letters Patent is hereby corrected as shown below:

At column 2, line 56, please delete "24b" and insert therefore, --24b:--.

At column 3, lines 50-51, please delete "2,3,3',4-biphenyltetracarboxylic" and insert therefore, --2,3,3',4'-biphenyltetracarboxylic--.

At column 7, line 50, please delete "our" and insert therefore, --out--.

At column 10, line 7, please delete "high)" and insert therefore, --high,--.

At column 10, line 64, please delete "Kyoristu" and insert therefore, --Kyoritsu--.

At column 11, line 12, in Claim 1, before "bubbling" delete "in".

Signed and Sealed this
Twenty-sixth Day of June, 2012

David J. Kappos
*Director of the United States Patent and Trademark Office*